(12) United States Patent
Simpson

(10) Patent No.: US 7,762,989 B2
(45) Date of Patent: Jul. 27, 2010

(54) METHOD AND APPARATUS FOR PREVENTING THE USE OF UNAUTHORIZED DISPOSABLE SETS IN INFUSION PUMPS

(75) Inventor: Peter C. Simpson, Glencoe, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 2 days.

(21) Appl. No.: 12/028,409

(22) Filed: Feb. 8, 2008

(65) Prior Publication Data
US 2009/0204075 A1 Aug. 13, 2009

(51) Int. Cl.
*A61M 1/00* (2006.01)
*A61M 37/00* (2006.01)

(52) U.S. Cl. .................. 604/151; 604/131
(58) Field of Classification Search .......... 604/151
See application file for complete search history.

(56) References Cited

U.S. PATENT DOCUMENTS

| | | | |
|---|---|---|---|
| 5,290,239 | A | 3/1994 | Classey et al. |
| 5,842,841 | A | 12/1998 | Danby et al. |
| 6,117,115 | A | 9/2000 | Hill et al. |
| 6,123,524 | A | 9/2000 | Danby et al. |
| RE37,074 | E | 2/2001 | Danby et al. |
| 6,600,418 | B2 | 7/2003 | Francis et al. |
| 6,635,033 | B1 | 10/2003 | Hill et al. |
| 2001/0040127 | A1 | 11/2001 | Donig et al. |
| 2002/0038392 | A1 | 3/2002 | De La Huerga |
| 2004/0104271 | A1 | 6/2004 | Martucci et al. |
| 2005/0277873 | A1 | 12/2005 | Stewart et al. |
| 2005/0277911 | A1 | 12/2005 | Stewart et al. |
| 2006/0224128 | A1* | 10/2006 | Lurvey et al. ............. 604/250 |

FOREIGN PATENT DOCUMENTS

| | | |
|---|---|---|
| WO | WO 03/030962 | 4/2003 |
| WO | 2005/118027 | 12/2005 |
| WO | 2005/118054 | 12/2005 |
| WO | 2006/083933 | 8/2006 |
| WO | 2007/041843 | 4/2007 |

OTHER PUBLICATIONS

International Search Report and Written Opinion for International Application No. PCT/US2009/032923 mailed on Apr. 24, 2009.

* cited by examiner

*Primary Examiner*—Nicholas D Lucchesi
*Assistant Examiner*—Jason Flick
(74) *Attorney, Agent, or Firm*—K&L Gates LLP

(57) ABSTRACT

A system and method for automatically delivering an infusate to a patient is disclosed. The system includes an infusion set and an infusion device. A signaling component disposed on an infusion set component identifies the infusion set and is encrypted for security. The encryption may include both an encryption algorithm and a valid number algorithm. A detection device operatively connected to the infusion device decrypts and detects the signaling component and identifies the infusion set. The infusion device is then configured to operate according to an administration protocol suitable for the infusion set and an infusion device, such as an infusion pump.

11 Claims, 2 Drawing Sheets

METHOD AND APPARATUS FOR PREVENTING THE USE OF UNAUTHORIZED DISPOSABLE SETS IN INFUSION PUMPS

CROSS REFERENCE TO APPLICATIONS

This application expressly incorporates by reference, and makes a part hereof, the following U.S. patent applications: U.S. Publication 2005/0277911, Ser. No. 10/855,873.

BACKGROUND

The present disclosure relates to an infusion delivery system and method. The infusion system and method includes a detection device which detects an encrypted signaling component or device on an infusate set in order to identify the set. The system is then configured to operate according to an administration protocol for the identified infusate set, the particular patient, other drugs being administered, the hospital practice, and so forth. The signal component or device may be optical (e.g. read a barcode), electrical, RFID, magnetic, chemical, ultrasonic, mechanical or combinations thereof.

Infusion treatment is a common medical practice for delivering a medicament to a patient. Infusion treatment typically entails delivering a fluid infusate, either parenterally or enterally, to a patient with an infusion device, most commonly an infusion pump. The infusate is typically provided by an infusion set having an infusate source, an infusate tube extending from the infusate source and a slide clamp adapted to receive the infusate tube. The slide clamp, which assists with infusate flow regulation, and the infusate tube when connected to the infusion pump place the infusate in fluid communication with the infusion pump.

Delivery of the infusate to the patient typically involves the physical and/or mechanical manipulation of the infusate tube by the infusion pump. Conventional infusion pumps customarily include parameters that may be adjusted in order to adapt to specific infusion set administration protocol delivery requirements. The parameters may include settings to accommodate the composition of the infusate, the physical and/or material properties of the infusate tube and the flow rate for effective infusate delivery, for example. The parameters may also include settings to accommodate the use of a special set compatible with a specific infusate, or to accommodate the use of a special set including a specific set component such as a particular valve or sensor.

As the number and sophistication of infusion set delivery requirements and infusion pump settings has increased, so too has the likelihood increased for a mismatch between the infusion set delivery requirements and the infusion pump settings. Such a mismatch may be highly injurious and potentially lethal to the infusion treatment patient. To further complicate matters, infusion pumps are typically undedicated, portable medical resources moved between different patients in a health care facility. Left unchecked, the infusion pump settings for one patient may be highly dangerous to a subsequent patient in need of the infusion pump. Relying on already overburdened health care professionals to ensure every infusion set delivery parameter is properly set on the infusion pump does not reduce the risk of mismatch between the infusion set requirements and the infusion pump settings to an acceptable level. What is needed is a better way to ensure that a particular infusion set is the correct one for use with a particular infusion device or pump, and preferably with a particular patient and infusion protocol.

SUMMARY

In accordance with the present disclosure, a system for delivering infusate to a patient is provided. The system includes an infusion device and an infusion set. The system further includes a slide clamp corresponding to the infusion set. A signaling component is disposed on the slide clamp. The signaling component is encoded with a key that includes an encryption algorithm and a valid number algorithm and identifies the infusion set. A detection device reads the signaling component, and subsequently generates a signal based on the encoded key and the identified infusion set. A controller, which is capable of decoding the key and is operatively connected to the infusion device, receives the signal. The controller is adapted to configure the infusion device to operate according to the particular infusion set and an administration protocol upon validating the infusion set. The use of an encoded key with an encryption algorithm and a valid number algorithm in the signal component adds a layer of security and prevents unauthorized use of infusion sets.

In accordance with one aspect of the present disclosure, the signaling component may be disposed on a surface of the slide clamp, within the slide clamp, or may be disposed both on and within the slide clamp. The signaling component may be affixed to the slide clamp as is commonly known in the art including adhesive attachment, heat bonded, ultrasonic welding, insert molded or by a swaged attachment.

In accordance with another aspect of the present disclosure, the detection device may be either a component of the infusion device or a remote detection device that may be positioned at a remote location relative to the infusion device. As a component of the infusion device, the detection device is positioned proximate to a port adapted to receive the slide clamp.

Alternatively, the remotely located detection device may further be a hand-held device, such as a personal data assistant, adapted to be portably maneuvered proximate to the slide clamp in order to scan the signaling component. The detection device may be operatively connected to the controller as is commonly known in the art including by such non-limiting examples as an infrared connection, a microwave connection, a radio frequency connection, an electrical connection, a Bluetooth connection, a LAN network connection, a WAN network connection, an Internet connection, a universal serial bus connection and combinations thereof.

In accordance with another aspect of the present disclosure, the signaling component may be an optical signaling component, an electrical signaling component, a radio frequency signaling component, a magnetic signaling component, a thermal signaling component, an ultrasonic signaling component, a mechanical signaling component and combination thereof. In an embodiment, the detection device may correspond to the type of signaling component. Thus, the detection device may be an optical detection device, an electrical detection device, a radio frequency detection device, a magnetic detection device, a thermal detection device, an ultrasonic detection device, a mechanical detection device, and combinations thereof.

In an embodiment, the optical signaling component may be a bar code, a reflective material, a fluorescent or phosphorescent material, a reflective foil, a metal component, a color, a translucent or transparent material, printing, etching, ink, an ink printed code, UV ink or pigment, infrared ink or pigment, adhesive ink, an adhesive, a burn mark, a laser mark, a heat marking, an arrangement of holes extending through the slide clamp, an arrangement of protrusions extending from a slide clamp surface, an arrangement of indentations disposed on a portion of a slide clamp surface, and an arrangement of protrusions and indentations disposed on a slide clamp surface, and combinations thereof.

The optical signaling component may be a bar code, such as a Universal Product Code, and may be detectable by a bar code reader. The optical signaling component may be an arrangement of holes extending through the slide clamp, an arrangement of protrusions and/or indentations on a surface of the slide clamp, detectable by an optical detection device having a light emitter and a light receiver such as a linear optical array or a laser light source. The optical signaling component may further be a color, an ink printed code, an ultraviolet ink printed code, or a reflective material with a respective optical detection device adapted to detect the color, the ink, the ultraviolet ink or the reflective material and identify the particular infusion set therefrom.

In accordance with a further aspect of the present disclosure, the signaling component is an electronic signaling component and the detection device is configured to detect the electronic signaling component. The electronic signaling component may be composed of an electrical conducting material having an electrical resistance. A particular infusion set may then be associated with, assigned to, or otherwise identified by the electrical resistance of the electronic signaling component. The detection device may then be suitably adapted to detect the electrical resistance and identify the infusion set based on the electrical resistance of the electronic signaling component. Detection may occur by contact between the electrical signaling component and the electrical detection device.

In accordance with another aspect of the present disclosure, the signaling component may be a radio frequency signaling component, a radio frequency tag, and the detection device is a radio frequency detector, a radio frequency interrogator. Information identifying the infusion set may then be preprogrammed into the memory of the radio frequency signaling component, as is commonly known in the art. As this radio frequency signaling component is capable of storing and conveying large amounts of data to the radio frequency detector, the radio frequency signaling component is particularly advantageous for use with infusion sets having detailed data or otherwise large amounts of infusion set delivery requirements.

In accordance with another aspect of the present disclosure, the signaling component may be an ultrasonic signaling component and the detection device is adapted to detect the ultrasonic signaling component and is an ultrasonic transducer. The ultrasonic signaling component has at least one property such as a density, a shape, a geometry and an orientation on/in the slide clamp. A property or a combination of properties of the ultrasonic signaling component may be varied to provide detection differentiation between ultrasonic signaling components. A distinct or particular infusion set may then be associated with or identified by each distinct ultrasonic signaling component.

In accordance with another aspect of the present disclosure, a slide clamp for use with an infusion device and an infusion set is provided. The slide clamp includes a body having an aperture adapted to receive the infusate tube of the infusion set. The slide clamp further includes a signaling component with a key that includes an encryption algorithm and a valid number algorithm, the signaling component configured to communicate information indicative of the infusion set to a detecting device operatively connected to the infusion device. The signaling component may be an optical signaling component, an electrical signaling component, a radio frequency signaling component, an ultrasonic signaling component, a magnetic signaling component as previously discussed.

The signaling component may be affixed to a slide clamp body surface as is commonly known in the art with a heat bond, adhesive material, ultrasonic weld, a press interference fit or a swaged attachment being choices. The signaling component may also include a plurality of legs corresponding to a plurality of openings disposed on a slide clamp surface.

A further aspect of the present disclosure is a method for delivering an infusate to a patient with an infusion set and an infusion device, the infusion set having a slide clamp component. The method includes steps of providing a signaling component on a component of the infusion set, the signaling component encoded with a key that includes an encryption algorithm and a valid number algorithm, configured with information indicative of the infusion set. The method also includes detecting the signaling component with a detection device and generating a signal, and decrypting and validating the signal. The method also includes steps of determining the infusion set identified by the signaling component, and operating the infusion device according to an appropriate administration protocol.

The signaling component may be disposed on any component of the infusion set, namely, the infusate source, the infusate tube, the injection site, the slide clamp, a catheter or other component. The infusion device, such as an infusion pump, is suitably adapted to detect the signaling component, decrypt the encoded key, validate the signaling component, and determine or otherwise identify the infusion set, and administer the infusion set using the infusion device according to an administration protocol. The signaling component may be an optical signaling component, an electrical signaling component, a radio frequency signaling component, an ultrasonic signaling component, or a magnetic signaling component. It is understood that the infusion device is suitably adapted to detect the signaling of each respective signaling component.

In an embodiment, the detection device determines the infusion set identified by the signaling device and generates a signal based on the infusion set. The signal may be sent to a controller operatively connected to the infusion device which configures the infusion device according to the signal.

The method may further include affixing the signaling component to a surface of the infusate source, the infusate tube, or the slide clamp by heat bonding, ultrasonic bonding, adhesively bonding or swaging. Alternatively, the signaling component may be insert molded within the interior of the slide clamp.

The method may further include detecting an optical signaling component, an electronic signaling component, a magnetic signaling component, a radio frequency signaling component, an ultrasonic signaling component a mechanical signaling component and combinations thereof, with a respective optical detection device, an electronic detection device, a magnetic detection device, a radio frequency detection device, an ultrasonic detection device a mechanical detection device and combinations thereof. The detection may occur proximate to the infusion device, within the infusion device or at a location remote from the infusion device.

These and other aspects and attributes of the present disclosure will be discussed with reference to the following drawings and accompanying description.

Additional features and advantages of the present disclosure are described in, and will be apparent from, the following Detailed Description of the disclosure and the figures.

DETAILED DESCRIPTION

Figure 1:
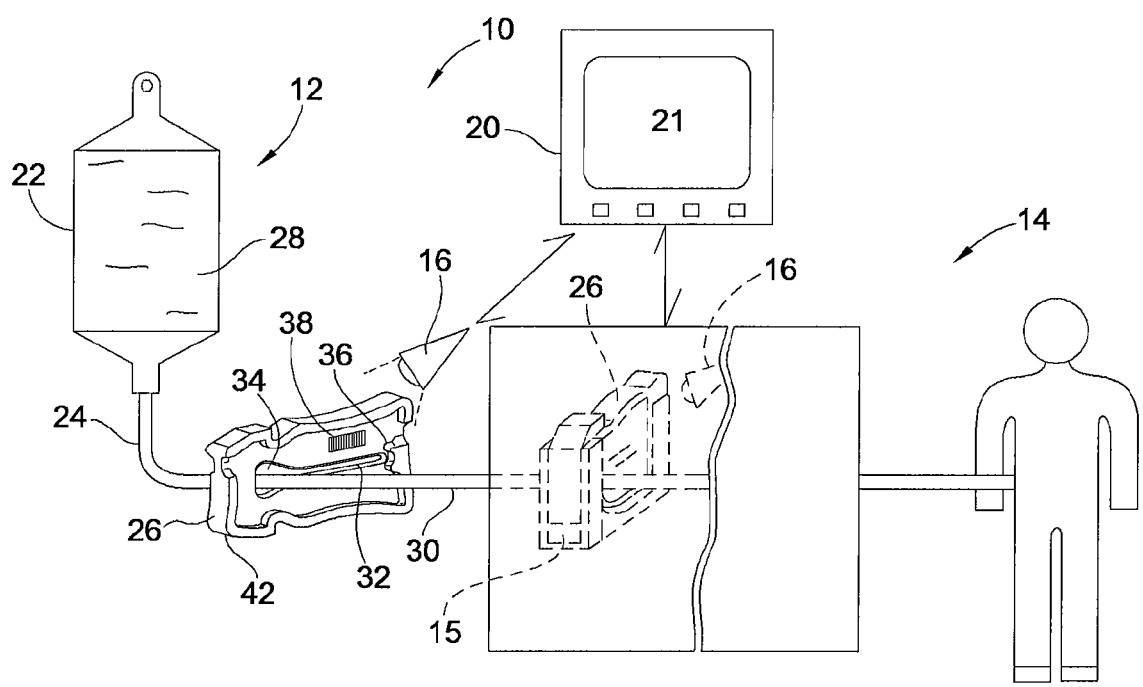
FIG. 1 is a schematic representation of an infusion delivery system in accordance with the present disclosure.

Referring to the figures generally, where reference numerals denote like structure and elements, and in particular to FIG. 1, an infusion delivery system 10 for delivering an infusate to a patient is shown. Infusion delivery system 10 includes an infusion set 12, an infusion device 14, a detection device 16 which generates a signal and a controller 20. Infusion set 12 includes an infusate source 22, an infusate tube 24 extending from infusate source 22, and a slide clamp 26.

Infusion device 14 may be any medical device capable of pumping a fluid into a patient as is commonly known in the art. Non-limiting examples of such devices include infusion pumps, cassette pumps and peristaltic pumps. Infusion device 14 may be a medical device capable of delivering fluids to a patient peristaltically. An example of a peristaltic infusion device is described in U.S. Pat. No. 6,123,524, which is hereby incorporated by reference. Examples of diffusion pump devices are described in U.S. Pat. No. RE37074, which is hereby incorporated by reference. Infusion device 14 further includes a port 15 for receiving slide clamp 26.

An infusate 28 is contained in infusate source 22. Infusate source 22 may be composed of glass or a rigid or flexible container composed of a polymeric material as is commonly known in the art. Infusate 28 may be any fluid or any fluid medicament that is administered by an infusion device. Examples of infusate 28 include, but are not limited to, saline or dextrose solutions, nutritional solutions, dialysis solutions, blood, blood components, blood substitutes and the like.

Infusate tube 24 extends from infusate source 22 and has a distal end 30 that is suitably adapted to connect to infusion device 14. Infusate tube 24 thereby provides a passage or a fluid connection enabling the delivery of infusate 28 to infusion device 14. The skilled artisan will appreciate that infusate tube 24 may be composed of a collapsible, flexible polymeric material. The composition of infusate tube 24 may the same as or different from the composition of infusate source 22.

Infusion set 12 further includes slide clamp 26 having an aperture 32 adapted to receive infusate tube 24. Aperture 32 includes a wide portion 34 and a narrow portion 36. One of ordinary skill in the art will appreciate that infusate may flow through infusate tube 24 when infusate tube 24 is received in wide portion 34 while infusate is prevented from flowing through infusate tube 24 when infusate tube 24 is received in narrow portion 36. Slide clamp 26 further includes a body 40 and a peripheral lip 42. Slide clamp 26 may be made from any rigid material including, but not limited to, wood, metal or a polymeric.

In an embodiment, slide clamp 26 may be made of a plastic material such as polypropylene, and is injection molded. Slide clamp 26 may also be made from a glycolized polyester such as PETG, co-polyester, an acetal resin such as DELRIN®, or any other suitable material that is capable of maintaining close manufacturing tolerances, can withstand pressures within infusate tube 24, and can withstand various sterilization techniques, including gamma and EtO sterilization, without impairing the functionality of slide clamp 26. In an embodiment, slide clamp 26 may be made from a polyethylene such as a high density polyethylene (HDPE) and optionally additives as explained more fully below.

A signaling component 38, which has been encrypted in an embodiment (described below in more detail), is disposed on slide clamp 26 by any suitable arrangement as is commonly known in the art. Consequently, "disposed" means that signaling component 38 may be located or otherwise positioned on, onto, in, within, or through slide clamp 26. The term "disposed" may further mean a position encompassing a combination of the aforementioned positions. Thus, a portion of signaling component 38 may be located on slide clamp 26 while another portion of signaling component 38 may be located within slide clamp 26 as will be described more fully below.

Signaling component 38 identifies infusion set 12. The signaling component may include any information related to, associated with or corresponding to the infusion set or to infusate 28. Consequently, the information may include any instructions, information, parameters, indicators, directions, identifiers, indicia, data, or directives associated with infusion set 12 and infusion device 14.

Non-limiting examples of information identified by the signaling component for use in an administration protocol include preferred infusion route type, infusion delivery type, infusate delivery temperature, infusate type, infusate tube composition, infusate flow rate, infusate quantity, infusate dosing unit, infusate dosing duration, infusate dosing volume, and infusion duration. This information is used by the infusion device, along with information concerning multiple infusate sources, multiple infusate mixing, secondary infusion administration, and combinations thereof. The administration protocol may also include patient information such as patient name, age, gender, height, weight, type of therapy, type of disease and type of condition of patient, for example.

Non-limiting examples of infusion route type include intravenous, parenteral, enteral, epidural, subcutaneous, intra-muscular, or other routes of medication administration. Infusion delivery type may identify dosing information such as continuous infusion, alternating infusions, sequencing infusions, tapering infusions, secondary infusate or piggyback parameters, infusate drip rate, and titrating infusions. Infusion delivery type may further include information regarding the composition of the infusate tube and physical properties such as tensile strength, modulus of elasticity, melting point or geometry, size, material type, or features or components of the tubing relating to appropriate drug solution compatibility or route of infusion. Infusate type may identify the composition of the infusate fluid or fluids or indicate whether a plurality of infusate fluids is to be delivered during the infusion session.

In addition, the administration protocol may include diagnostic information. The diagnostic information may be used to perform diagnostic tests or routines on the infusion device or any other component of the infusion system. For example, a diagnostic infusion set may include an infusate source containing a particular fluid to be used in the testing, wherein expected operational parameters of the infusion device based on the particular fluid may be used as a diagnostic benchmark.

The information encoded on the infusion set is typically predetermined information represented by one or more alpha-numeric characters, but may be representable by other identifiers such as a binary code or UPC code or some other engineered code, as is known in the art. The alpha-numeric characters represent information to be sent to the infusion device. Upon reception of a signal, controller 20 is programmed to recognize the predetermined information represented by the alpha-numeric characters. Controller 20 then configures infusion device 14 according to these predetermined parameters.

For example, an alpha-numeric representation of "12" may be predetermined to identify a standard parenteral saline solution of 500 ml, and an administration protocol may require a flow rate of 2.6 ml/min. Upon detection of the alpha-numeric representation "12" by detection device 16 and subsequent reception of the signal carrying the alpha-numeric representation of "12" by controller 20, controller 20 processes the infusion set information from the signal and configures infusion device 14 to the protocol settings denoted for infusion with an infusate designated by the alpha-numeric character "12" (i.e., the controller initiates the parenteral tube port and sets the pump and timing components for a flow rate of 2.6 ml/min). System 10 is adapted to identify from one to about 64 or more different predetermined administration protocols.

Detection device 16 of system 10 may be any device capable of decrypting (described below in more detail) and detecting signaling component 38 as is commonly known in the art. Detection device 16 detects or otherwise determines the infusion set identified by signaling component 38. Detection device 16 may be a component of or otherwise be integral to infusion device 14. Alternatively, detection device 16 may be located at a location remote from infusion device 14. Detection device 16 may also be a portable detection device. As a portable detection device, detection device 16 may be removable from a housing of infusion device 14.

Upon detection of signaling component 38, detection device 16 generates a signal that is based on the infusion set identified by the signaling component. Detection device 16 subsequently sends the signal to controller 20. Upon reception of the signal, controller 20 deciphers the signal, identifies and interprets the particular infusion set. Controller 20 is operatively connected to infusion device 14 and is further adapted to configure infusion device 14 to operate according to an administration protocol designated for the particular patient, other drugs being administered, and so forth.

Controller 20 includes a processor to process the infusion set information contained in the signal. Controller 20 may be a component of infusion device 14. Alternatively, controller 20 may be located at a location remote from infusion device 14. Controller 20 may further include a display 21 that displays and/or prompts or otherwise notifies information regarding the infusion set and also the administration protocol to a health care professional or the patient.

In an embodiment, the slide clamp 26, which includes the signaling component 38, serves as a key when the infusion set 12 is loaded into the infusion device 14. The key on each infusion set 12 is encrypted for added security. One method of encryption in the infusion system 10 is to place the encrypted key onto the infusion set 12 as an embedded RFID tag (e.g. signaling component 38) on slide clamp 26. In another embodiment, a bar code printed on the slide clamp 26 may be used. A detection device 16 (e.g. optical reader) reads and deciphers the bar code. It is noted that the key is not limited to RFID tags and bar codes, but may be in any form readily understood to the skilled artisan.

One encryption/decryption method is in the form of number verification. The number of keys would not be sequential, and would be drawn from a large pool of numbers such that a small percentage of the total pool of numbers would be valid, e.g., 2 to 5%. In order to determine whether a number is valid, the system could use a one-time encryption (e.g. where a number is valid only once) or an encryption algorithm. Prior to the start of each infusion, the infusion device 14 (i.e. pump) would read the encrypted infusion set ID using the detection device 16. Only infusion sets with an authenticated ID number would be valid. In the case of a one-time encryption method, the validated number is only used once, which prevents the re-use of sets, as well as the copying of a valid number from one set to another, unauthorized set. Use of the one-time comparison list in the pump eliminates the need for long-term storage of the numbers. For example, the list may be discarded after a set number of infusions. This ensures that sets with either cloned or randomly generated numbers could not be reliably used, and prevents counterfeiters from easily manufacturing products. Benefits include, for example, eliminating use of generic uncoded sets, re-use of sets, use of unknown counterfeit sets, and reducing the intentional use of counterfeit sets.

In another embodiment, each infusion set 12 is encoded with a public/private key encrypted code and the encrypted number, after being read, is sent to a central server for decoding and verification. The central server is connected, for example, via a network, to the infusion system 10. The central server then responds with a signal indicating that the number is or is not verified. Use of a central server allows for more computationally complex coding and the use of large one-time-use look-up tables of valid numbers. Alternatively, instead of using a central server, authentication and verification could occur within the infusion system 10. In this case, each pump includes a decryption algorithm and a valid number comparison. The pump then verifies whether the encoded key is valid. It is readily understood by the skilled artisan that encryption/decryption is not limited to a central server and/or pump, but could occur using any device within or connected to the infusion system 10. The use of only certain "valid" numbers prevents unauthorized use even if the encoding key is broken.

Additionally, use of a central server provides additional processing power and memory space beyond that found in the pump. As noted, the encrypted number could also be decrypted by the pump (i.e. infusion device 14), and the number processed by an encrypted algorithm that determines the validity of the decrypted number and compares it to a list of used numbers. It is readily understood that the encryption/decryption method employed could be any known by the skilled artisan and is not limited to the described embodiments.

Significantly, use of an encryption/decryption method prevents unintended use of the infusion sets, for example, by: preventing use of generic sets since a key is required; preventing unlawful use of encrypted data and copying of data; and preventing clones or counterfeit products.

Figure 2:
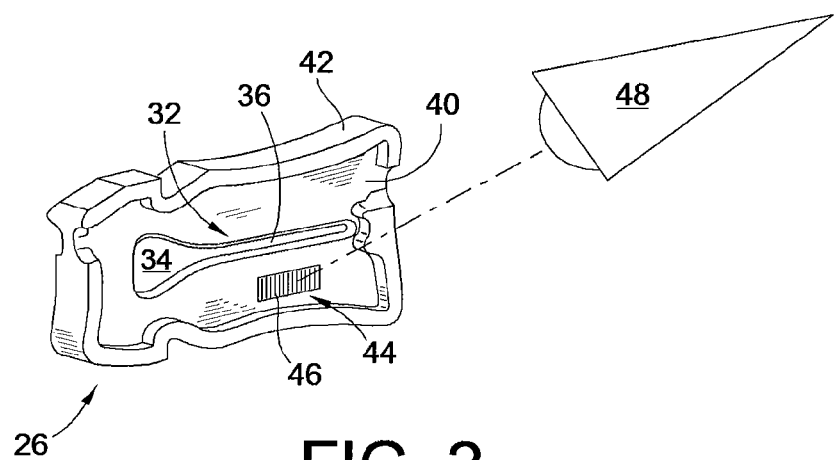
FIG. 2 is a perspective view of a slide clamp having an optical signaling component and an optical detection device in accordance with the present disclosure.

In accordance with one aspect of the present disclosure, signaling component 38 is an optical signaling component as shown in FIG. 2. Non-limiting examples of suitable optical signaling components include a bar code, a reflective material, a fluorescent or phosphorescent material, a reflective foil, a metal component, a color, a translucent or a transparent material, printing, etching, ink, an ink printed code, ultraviolet (UV) ink or pigment, infrared (IR) ink or pigment, adhesive ink, an adhesive, a burn mark, a heat marking, a laser mark, an arrangement of holes extending through the slide clamp, an arrangement of protrusions extending from a slide clamp surface, an arrangement of indentations disposed on a portion of a slide clamp surface, and an arrangement of protrusions and indentations disposed on a slide clamp surface. Regardless of the specific embodiment of the optical signaling component, it is understood that detection device 16 is suitably adapted to detect the optical signaling component.

In accordance with one aspect of the present disclosure, FIG. 2 depicts an optical signaling component 44 and may be a bar code 46. Bar code 46 may be any bar code capable of being encoded with the infusion set information as is commonly known in the art with a Universal Product Code (UPC). Bar code 46 identifies an alpha-numeric character which represents a code designating the particular infusion set and its identifying code. A bar code reader 48 may detect bar code 46, generate a signal based on the infusion set and send the signal to controller 20. Bar code reader 48 may or may not be a component of infusion device 20. Bar code reader 48 is a portable device electronically connected to controller 20.

Figure 3:
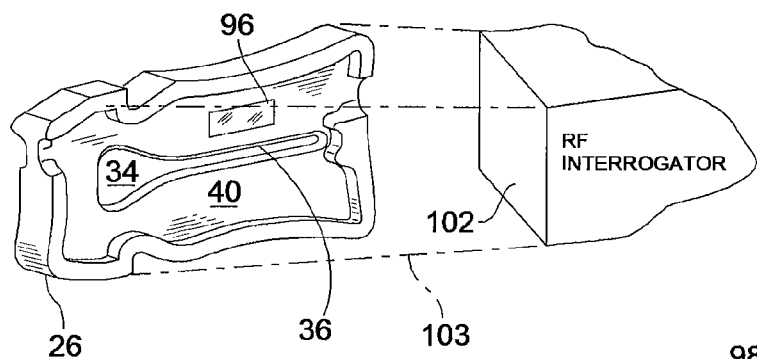
FIG. 3 is a perspective view of a slide clamp having a radio frequency signaling component and a radio frequency detection device in accordance with an alternate embodiment of the present disclosure.

In another aspect of the disclosure, the signaling component may be a radio frequency (RF) signaling component. The radio frequency signaling component is a radio frequency identification (RFID) tag 96 as shown in FIG. 3. RFID tag 96 is capable of receiving, storing and transmitting information as is commonly known in the art. RFID tag 96 may include an antenna, circuitry for processing RF signals, a microprocessor, memory, and, optionally, a power supply. Information identifying the particular infusion set is entered into RFID tag 96. In a further embodiment, the RFID tag may be a chipless RFID tag. The chipless RFID tag may include antennae printed on a surface of the slide clamp or embedded in the slide clamp interior.

Figure 4:
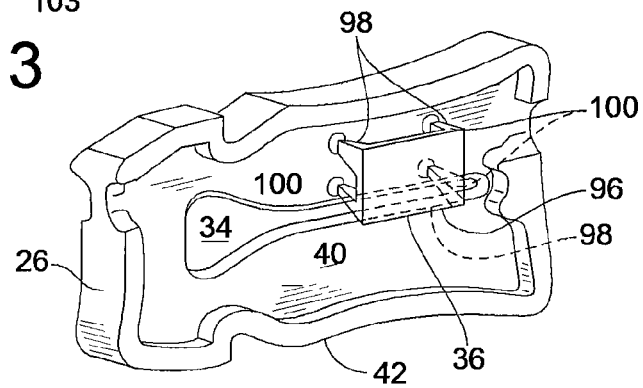
FIG. 4 is a perspective view of another embodiment of the slide clamp of FIG. 3 with a different radio frequency signaling component.

RFID tag 96 may be affixed to a surface of slide clamp 26 with an adhesive material or a heat bond as is commonly known in the art. RFID tag 96 includes legs 98 which may be inserted into corresponding holes 100 disposed on body 40 to affix RFID tag 96 to slide clamp 26 as shown in FIG. 4. Legs 98 may be secured in holes 100 with an adhesive material, friction fit, rivets, screws or with a swaged arrangement whereby legs 98 are bent after insertion into holes 100. Alternatively, tag 96 may be insert molded into the interior of slide clamp 26.

RFID tag 96 may be a passive device or an active device. As a passive device, an RFID tag transmits a signal only upon reception of an RF interrogation signal utilizing operating power generated from the RF interrogator. As an active device, an RFID tag is configured with its own power supply and thereby capable of transmitting a signal independently. As passive RFID tags are smaller and lighter than active RFID tags, the RFID tag 96 may be for example a passive RFID device.

In this embodiment of the disclosure, the detection device is an RF detector adapted to detect RFID tag 98. The RF detector is an RF interrogator 102 as shown in FIG. 3. RF interrogator 102 typically includes an antenna, a transceiver for transmitting an interrogation signal to and receiving a response signal from the RFID tag, and a decoder for reading the encoded information in the signal from the RFID tag. RF interrogator 102 generates an electromagnetic field 103 at a predetermined frequency. When RFID tag 96 enters the field, an electric current is induced providing power to RFID tag 96 and modulating the electromagnetic field to transmit the infusion set data stored in the memory of RFID tag 96 back to RF interrogator 102. RF interrogator 102 then decodes this data and transmits the infusion set data with the signal to controller 20.

A system including RFID tag 96 and RF interrogator 102 provides several advantages. A line-of-sight arrangement between signaling component 96 and RF interrogator 102 is not necessary for detection to occur. Consequently, RF interrogator 102 is well-suited to be located remote from controller 20, or serve as a portable or a hand-held detection device. It is understood, however, that RF interrogator 102 may be a component of infusion device 14.

Moreover, as no contact between signaling component 96 and RF interrogator 102 is required for detection, conditions otherwise deleterious to proper detection of the signaling component are eliminated. For example, a wet slide clamp or fluid, dust, dirt, or any other physical impediment disposed upon the slide clamp have no impact on the proper detection of RFID tag 96 by RF interrogator 102.

The skilled artisan will further recognize that the large memory capacity of RFID tags allows for more information to be carried by RFID tag 96 and consequently conveyed to RF interrogator 102. As a result, the infusion set data stored in RFID tag 96 may contain a substantial amount of detailed and/or sophisticated information. For example, RFID tag 96 typically has the capacity to carry more administration instructions and/or operating parameters for infusion device 14 than some of the previously discussed signaling components.

The present disclosure contemplates that detection device 16 may be a component of infusion device 14 as shown in phantom in FIG. 1. In this arrangement, detection device 16 is located proximate to port 15 and adapted to detect signaling component 38 when slide clamp 26 is secured in port 15. Alternatively, detection device 16 may be a remote detection device located at a location remote from infusion device 14. As a remote detection device, detection device 16 may be operatively connected to infusion device 14 by any suitable connection as is commonly known in the art including non-limiting examples such as an infrared connection, a microwave connection, a radio frequency connection, an electrical connection, a Bluetooth connection, a LAN network connection, a WAN network connection, an Internet connection, a universal serial bus connection and combinations thereof. The remote detection device may be a hand-held detection device such as a personal data assistant, for example.

Figure 5:
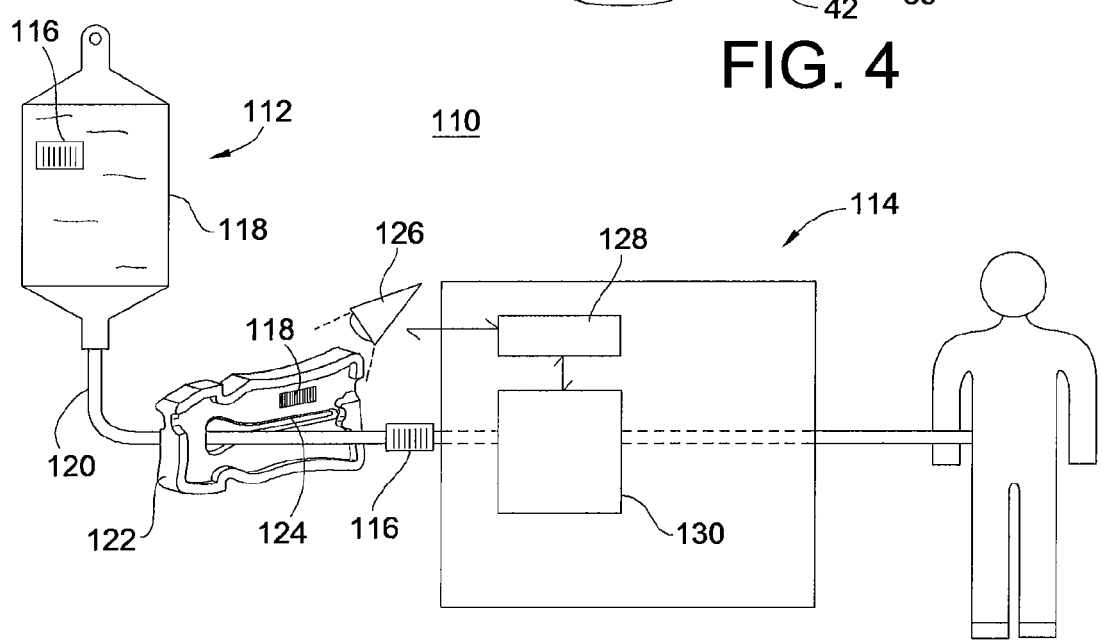
FIG. 5 is a schematic view of an embodiment of the infusion delivery system in accordance with the present disclosure.

In another embodiment of the present disclosure, infusion system 110 includes an infusion set 112, an infusion device 114 and a signaling component 116 as shown in FIG. 5. Infusion set 112 includes an infusate source component 118, an infusate tube component 120 extending from infusate source component 118 and a slide clamp component 122 with an aperture 124 adapted to receive infusate tube component 120.

Signaling component 116 may be disposed on at least one component of infusion set 112. Signaling component 116 includes information indicative of infusion set 112 as previously described. Infusion device 114 is adapted to detect signaling component 116 and determine the administration protocol indicated by signaling component 116. Infusion device 114 may then be selectively operated or otherwise configured according to a desired administration protocol. Infusion device 114 is automatically configured to operate according to the administration protocol. It is understood that infusion device 114 may include a control panel or similar user interface that displays the identified infusion set and enables an operator to manually select or adjust the operating parameters according to an appropriate administration protocol for the particular infusion set, the patient, instructions from a medical professional, and so forth.

Signaling component 116 may be disposed on any component of infusion set 112. Thus, signaling component 116 may be disposed on infusate source component 118, infusate tube component 120, or slide clamp component 122 as shown in FIG. 5. Signaling component 116 may be disposed on a surface of the infusion set component where the infusion set component is infusate source component 118 or infusate tube component 120. Signaling component 116 may include any type of signaling component such as an optical signaling component, an electronic signaling component, a magnetic signaling component, a radio frequency signaling component, and an ultrasonic signaling component as previously discussed.

Infusion device 114 includes a detection device 126 adapted to detect signaling component 116. Detection device 126 may be disposed on an exterior surface of infusion device 114. This enables a health care professional or the infusion patient to place signaling component 116 within the detection zone of detection device 126 regardless of which infusion set component is carrying signaling component 116.

Alternatively, detection device 126 may be a remote and/or a hand-held detection device as previously discussed. The remote/hand-held detection device is sufficiently portable to be moved within the vicinity of any component of infusion set 112 in order to detect a signaling component disposed thereon. Detection device 126 may be operatively connected to a controller 128 or directly to an infusion pump 130 as previously discussed.

It should be understood that various changes and modifications to the presently described embodiments will be apparent to those skilled in the art. Such changes and modifications can be made without departing from the spirit and scope of the present disclosure and without diminishing its intended advantages. It is therefore intended that such changes and modifications be covered by the appended claims.

What is claimed is:

1. A system for delivering infusate to a patient, the system comprising:
    an infusion device;
    an infusion set;
    a slide clamp corresponding to the infusion set;
    a signaling component disposed on the clamp and encoded with a key, the key including an encryption algorithm and a valid number from a valid number table, wherein: (i) the encryption algorithm encrypts the valid number, and (ii) the signaling component identifies the infusion set using the encrypted valid number of the encoded key;
    a detection device to read the signaling component and configured to generate a signal, the detection device operable with a decryption algorithm, to allow:
        (a) the decryption algorithm to determine a decrypted valid number by decrypting the encrypted valid number from the encoded key, and
        (b) the decrypted valid number to be compared to the valid number table; and
    wherein, based upon the decrypted valid number comparison, the signal generated by the detection device either validates or rejects use of the infusion set with the infusion device.

2. The system of claim 1 wherein the infusion device is an infusion pump.

3. The system of claim 1 wherein the signaling component is selected from the group consisting of an optical signaling component, an electrical signaling component, a radio frequency signaling component, a magnetic signaling component, a thermal signaling component, an ultrasonic signaling component, a mechanical signaling component, and combinations thereof.

4. The system of claim 1 wherein the signaling component is an optical signaling component selected from the group consisting of a bar code, a reflective material, a fluorescent material, a metal component, a color, a translucent material, printing, etching, ink, an ink printed code, ultraviolet pigment, infrared pigment, a heat marking, a laser mark, an arrangement of translucent areas, a protrusion extending from a slide clamp surface, an indentation disposed on a slide clamp surface, and combinations thereof.

5. The system of claim 1 further comprising a controller to receive the signal and operatively connected to the infusion device, the controller adapted to configure the infusion device to operate according to an administration protocol.

6. The system of claim 1 wherein the detection device reads the signal component and generates a signal corresponding to the read signal component.

7. The system of claim 6 wherein the detection device sends the generated signal to one of the infusion device or a central server for decoding.

8. The system of claim 7 wherein the generated signal is decoded by the infusion device or the central server, and the infusion set is validated or rejected.

9. The system of claim 8 wherein decoding is accomplished using a decryption algorithm and a valid number algorithm.

10. The system of claim 6 wherein the detection device is part of the infusion device.

11. The system of claim 6 wherein the detection device is remotely located from the infusion set.

* * * * *